(12) United States Patent
Filz (10) Patent No.: US 10,413,715 B2
(45) Date of Patent: Sep. 17, 2019

(54) DEFENSIV

(71) Applicant: Jonathan David Filz, Charlotte, NC (US)

(72) Inventor: Jonathan David Filz, Charlotte, NC (US)

(*) Notice: Subject to any disclaimer, the term of this patent is extended or adjusted under 35 U.S.C. 154(b) by 0 days.

(21) Appl. No.: 15/232,670

(22) Filed: Aug. 9, 2016

(65) Prior Publication Data
US 2017/0065808 A1    Mar. 9, 2017

Related U.S. Application Data

(60) Provisional application No. 62/203,524, filed on Aug. 11, 2015.

(51) Int. Cl.
| | | |
|---|---|---|
| *A61M 25/00* | (2006.01) | |
| *A61M 39/18* | (2006.01) | |
| *A61M 39/16* | (2006.01) | |

(52) U.S. Cl.
CPC .......... *A61M 39/18* (2013.01); *A61M 39/165* (2013.01)

(58) Field of Classification Search
CPC ............... A61M 39/165; A61M 39/18; A61M 39/1011; A61M 39/20; A61M 39/12; A61M 39/1066; A61M 39/10; A61M 2039/0009; A61M 2039/1077; A61M 2209/00; A61M 2025/0006; A61M 25/02; A61M 2025/0206

USPC ........................................................ 604/523
See application file for complete search history.

(56) References Cited

U.S. PATENT DOCUMENTS

| | | | | |
|---|---|---|---|---|
| 5,165,874 | A * | 11/1992 | Sancoff ............ | A61M 5/14228 128/DIG. 12 |
| 5,817,067 | A * | 10/1998 | Tsukada ................ | A61F 2/0018 604/256 |
| 2010/0069830 | A1 * | 3/2010 | Grigorov .......... | A61M 5/14248 604/67 |
| 2013/0331635 | A1 * | 12/2013 | Hoffman .............. | A61N 5/1007 600/5 |
| 2014/0135738 | A1 * | 5/2014 | Panian .................. | A61M 39/20 604/535 |
| 2015/0174315 | A1 * | 6/2015 | Rebergue ............... | A61M 5/007 600/431 |

\* cited by examiner

*Primary Examiner* — Jason E Flick
(74) *Attorney, Agent, or Firm* — G. Spencer Lueders (57) ABSTRACT

This invention is an apparatus for physically enclosing access ports on intravenous (IV) tubing to defend against bacterial contamination. In one configuration, the invention encapsulates an IV manifold and contains a sliding door mechanism to allow access to the ports. In another configuration, the invention covers an individual access port and contains a flip-top cap to allow access to the port. In either configuration, a chemical solution can optionally be included on either the cushioned strip or the cushioned disc to provide additional bacterial protection to the ports.

6 Claims, 8 Drawing Sheets

DEFENSIV

STATEMENT REGARDING FEDERALLY SPONSORED RESEARCH OR DEVELOPMENT

Not Applicable

BACKGROUND

Multiple studies have documented the staggering prevalence of Hospital Acquired Infections (HAI's). When compared to automobile crash fatality data, hospitalized patients are 2.4 times more likely to die from a HAI than from a road accident. The Center for Disease Control (CDC) ranks HAI's among the top 10 leading causes of death in the U.S. In fact, the CDC also states that nearly 2 million HAI's are contracted each year, leading to nearly 100,000 deaths. Of these 2 million HAI's, approximately 850,000 are classified as Catheter-Associated Infections (CAI's).

According to CDC surveillance criteria, 50,000 of these CAI's are further categorized as Catheter Associated Bacteremia's (CAB's). The case fatality rate for CAB's is more than 20% (10,000 deaths/50,000 cases) with an attributable mortality rate of 35%. Essentially, any time a patient undergoes intravenous therapy and develops complications that result in death, 35% of that patient's death can be attributed to the presence of an intravenous catheter. CAB's primarily occur from poor aseptic technique, ultimately leading to contamination of intravenous catheter access ports during medication administration.

Besides the staggering mortality statistics, the healthcare costs for treating HAI's are monumental. Just one patient with a CAI can increase treatment costs by $45,800 and increase their hospital length of stay by an average of 10.4 days. Overall, it is estimated that HAI's cost acute-care hospitals between $35 and $45 billion annually. Furthermore, total direct, indirect, and non-medical social costs of HAI's are estimated at around $96 to $147 billion annually, including loss of work, legal costs, and other patient factors.

As recommended by the CDC, more than 80% of intravenous access devices are needle-free, meaning they use a Needle-less Connector (NC), also known as a port, or NC port. NC's provide easy access points for medication infusion connections or injections. A syringe can easily be screwed onto the NC, then medications can be delivered via the venous blood system (either peripherally or centrally).

Although the NC is convenient to use, it is not without an inherent problem. The NC port is among the many documented vectors for microbe transmission and listed as the primary source for most pathogens causing endemic CAI's. Bacterial colonization of the NC port can lead to bloodstream infections known as Catheter Associated Bloodstream Infections (CABSI) or Central Line Associated Bloodstream Infections (CLABSI), both being specific types of CAB's.

Over the years, needle safety concerns for the healthcare worker has led to the current design of the NC. Although the NC has effectively halted accidental needle sticks by healthcare workers, it has posed a new problem—contamination of the NC itself. Risk factors for contamination include air contaminants, contamination from the patient's own flora (clothing, bedding, dressings), or from healthcare workers' hands during medication administration. Human error of the healthcare worker results from poor adherence to aseptic technique secondary to inconsistent staff education and training. Even basic hand-washing compliance rates are between 25-50%. Unfortunately, very few procedural changes have been implemented that protect the access ports and address the problem of human error.

Furthermore, the design of the NC port itself also plays a crucial role in microbe transmission. Current designs are not intuitive, therefore the intuitive sense to disinfect the port surface prior to medication administration is lost. Just one omission of disinfecting the port prior to access permits bacterial entry, attachment, and biofilm formation, allowing bacteria to strengthen prior to release into the bloodstream. Once a catheter port is contaminated, infections result from bacterial seeding during manipulation of the port or catheter junctions. IV tubing may also become inadvertently contaminated when allowed to drape onto the floor or when placed next to the patient in bed. Once contaminated, bacterial ingress into the catheter lumen is considered the cause of 50% of post-insertion catheter-related infections.

The Association for Professionals in Infection Control defines disinfection as a process to eliminate micro-organisms with the use of liquid chemicals or pasteurizing. This process is only effective by having proper contact time with the intended surface. CDC recommendations and the Infection Nurses Society state that the clinician should minimize contamination risk by disinfecting the access ports using friction with and appropriate disinfectant (70% alcohol, chlorhexidine, or povidone iodine) prior to each access of an intravascular device.

Multiple studies demonstrate that infections are drastically lowered or eliminated by disinfecting the access ports prior to use, or by even covering the access ports with an anti-microbial cap when not in use. The disadvantages of the anti-microbial cap requirement is that they can be cumbersome to screw on, and they are a one-time use item. Currently, intravenous tubing sets require multiple anti-microbial caps. In turn, this necessitates a rather large supply of them to be readily available during routine use. This only further decreases the likelihood of adherence to disinfection compliance.

Alcohol wipes are the most commonly used item to disinfect the access port. However, these wipes have been proven both effective and ineffective at disinfection times ranging from 5-60 seconds. Like the protective caps, a ready supply of wipes is required for effectiveness, but they can easily be forgotten at the bedside by the clinician. Isopropyl alcohol combined with chlorhexidine is more effective than either agent alone, but the effectiveness is only achieved after the liquids have dried. When these ports are utilized, the reality is that not every clinician swabs, or allows for adequate drying time of these agents for a number of reasons. Non-compliance can result from excessive workloads, increasing age of the clinician, the workplace culture, emergency situations, and failure to simply bring alcohol wipes to the bedside.

Currently, the problem of port contamination is only being addressed from a circumferential perspective. Conclusions in the literature continue to simply suggest that healthcare workers maintain vigilance with proper hand hygiene, alcohol swabbing, and until just recently, adding a protective cap to the IV port. However, even when using this protective cap, the port is still required to be cleaned after cap removal with an alcohol swab prior to use. Another problem is that no specific phase of patient care is ever identified as the sentinel cause of an HAI. For example, a blood-stream infection from a port contaminated pre-operatively, or even during surgery, may not reveal itself until days later. Therefore, real-time feedback of when the port was contaminated cannot be obtained.

Throughout a patient's surgical experience, multiple nurses as well as anesthesia personnel will have accessed that patient's IV ports multiple times while injecting medications. Since the pre-operative phase of care is where the potential for contamination is first encountered, it is imperative that the focus of port contamination should be shifted to initial patient contact and the environment that the IV ports are exposed to. This is where patients get their IV needle inserted, the intravenous tubing is taken out of its sterile packaging, spiked into a bag of fluids, and is then connected to the IV catheter. As the tubing and access ports are lying next to the patient, they are already rendered contaminated. This is because there is no physical barrier in place that keeps the individual ports free from the bacteria-ridden environment. More times than not, the patient will take their IV bag and tubing to the restroom with them, thus dragging the tubing and access ports along the floor. Once back in bed, the ports are further exposed to the patient's own flora and their bedding. All of these bacterial environments are encountered prior to the patient even going to the operating room (OR), posing a significant risk of contamination from the outset.

Anesthesiologists and Nurse Anesthetists are one of the first providers that patients encounter. Therefore, common sense dictates that anesthesia personnel can and should play an active role in the prevention of HAI's. When a patient is prepped for surgery, the Anesthetist starts a free-flowing IV line and administers several pre-operative medications (sedatives, antibiotics, and anti-nausea medications) via the NC ports prior to transfer to the OR. Anesthesia providers are also in frequent contact with the patient's skin and mucosa during surgery, and repeatedly access the bloodstream while administering medications, fluids, and obtaining blood samples. During surgery, the access ports are also often left exposed. This can allow direct contact to blood, urine, fecal matter, and gastric fluids. Many times the main manifold hub even inadvertently falls onto the OR floor, further exposing the patient to a host of bacteria. Also, at critical moments, medications need to be given rapidly, and it is not feasible to swab access ports and wait for a drying time prior to administering critical medications.

Although anesthesia safety itself has improved over the past decades, studies have found that anesthesia professionals have the lowest compliance with hand hygiene recommendations across all medical specialties. Major bacterial pathogens have been identified on the hands of Anesthetists even prior to patient contact. These pathogens can ultimately lead to a contaminated work environment. A recent study showed that transmission of bacteria to IV access ports occurs 32% more frequently and that transfer of certain bacteria occurs in less than 5 minutes during anesthesia care. In a typical anesthesia procedure, there are up to 60 opportunities for hand hygiene, although the typical anesthesia provider performs hand hygiene less than once per hour during a procedure.

After surgery, the patient is taken to the recovery unit. Once there, the current procedure is for the existing free-flowing IV tubing to be changed out for tubing that functions on an IV pump, thus regulating the amount of fluids that a patient receives. Like the pre-operative scenario, this new tubing is exposed to pathogens on the patient, the bed, bandages, etc. Then, post-operative medications are given via potentially contaminated IV ports. After the recovery phase, the patient is transferred to a hospital bed. This is where the patient will encounter yet another team of nurses who will provide more medication injections. This will continue exposing the patient to the possibility of developing an infection directly related to routine access of the IV tubing. The only defense that currently exists is the clinician that rigorously adheres to protocol; basic hand-washing technique, swabbing access ports, waiting for a dry time, and then re-covering the ports with a new protective cap. However, as the literature shows, this is not a realistic expectation.

Since patients move through each phase of care within a matter of hours, one can easily see that the specific moment of port contamination can be difficult to identify. Therefore, it is imperative that the potential for contamination be addressed from a ground-zero approach. This invention is designed to provide both a physical and chemical layer of protection in a unique way that does not currently exist. This will help the clinician to keep IV ports disinfected throughout a patient's hospital stay. With its innovative design, it comprehensively addresses the contaminations risks inherent in the pre-operative, surgical, and post-operative phases of care. Use of this invention will also serve as a reminder to the clinician and the patient, that prevention of infection is a continuous, real-time process. The end goal is to reduce the number of IV port contaminants, and ultimately reduce the number of CAI's seen within healthcare today.

For the foregoing reasons, there is a need for a device which physically covers the IV ports and also can provide continuous chemical disinfection.

SUMMARY

The present invention is directed to an apparatus that satisfies the need for a device which physically covers ports on IV lines and can also provide continuous chemical disinfection. A device having features of the present invention comprises an enclosure which in one embodiment completely surrounds an IV manifold and preferably contains a sliding door mechanism to allow access to the ports. This enclosure preferably includes one or more slots and/or grooves on the inside to properly constrain the IV tubing. In one embodiment, the enclosure can be hinged to allow a clam-shell-like opening and closing action in order to attach and detach from the IV tubing. In one embodiment, one side of the sliding door mechanism can have a cushioned strip to which a chemical solution can be applied to or embedded with in order to disinfect the ports when the sliding door mechanism is in a closed position.

A device having features of the present invention could also comprise a shroud with a flip-top cap for use with single IV ports. This shroud can attach to the top of a single IV port either via a snug, friction based attachment, or a snap connection using plastic tabs. The flip-top cap can be opened to allow access to the port. This flip-top cap will be physically connected to the rest of the shroud via a connector band so that it doesn't get lost while the port is being accessed. The underside of the flip-top cap can have a cushioned disc to which a chemical solution can be applied to disinfect the port when the flip-top cap is in the closed position.

BRIEF DESCRIPTION OF THE DRAWINGS

These and other features, aspects, and advantages of the present invention will become better understood with regard to the following description, appended claims, and accompanying drawings where:

DESCRIPTION

In the Summary above and in the Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and the invention generally.

The term "comprises" and grammatical equivalents thereof are used herein to mean that other components are optionally present. For example, an article "comprising" components A, B, and C can consist of components A, B, and C, or can contain not only components A, B, and C but also one or more other components.

One purpose of the present invention is to provide a physical enclosure to prevent bacteria from coming into contact with intravenous tubing access ports. In at least one embodiment shown in FIGS. 1-8, physical protection of one or more intravenous tubing access ports 60 is ensured when each access port 60 is housed within a clam-shell style or pill-shaped body 20. In an alternate embodiment shown in FIGS. 10-15, the access port 60 is housed within a frusto-conical or funnel-shaped body 28. By way of definition and not limitation, the terms "clam-shell" and "pill-shaped" are visual descriptions of one embodiment of the present invention. The physical shape of the body 20 is not limited to these visual descriptions, and could take on any number of alternative shapes without detracting from the function or purpose of the present invention, including without limitation square, rectangular, oblong, or any other shape that encloses an intravenous manifold and allows syringe access to one or more intravenous ports.

Figure 1:
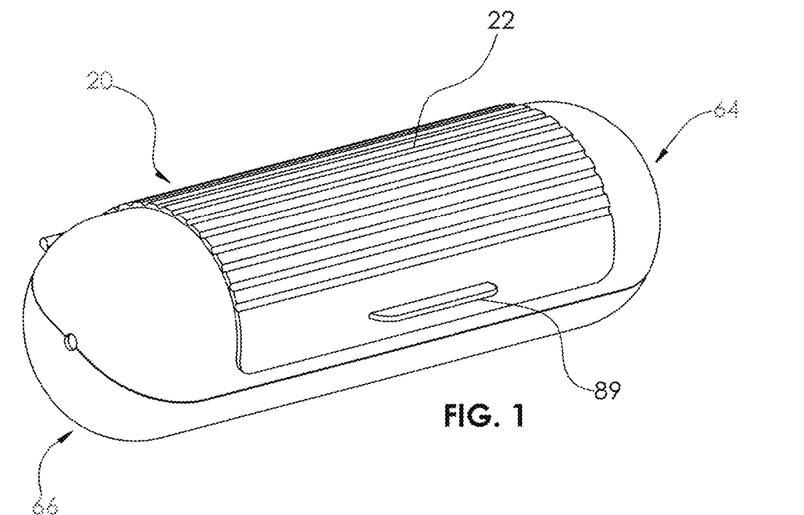
FIG. 1 shows a perspective view of an apparatus embodying features of the present invention.
Figure 2:
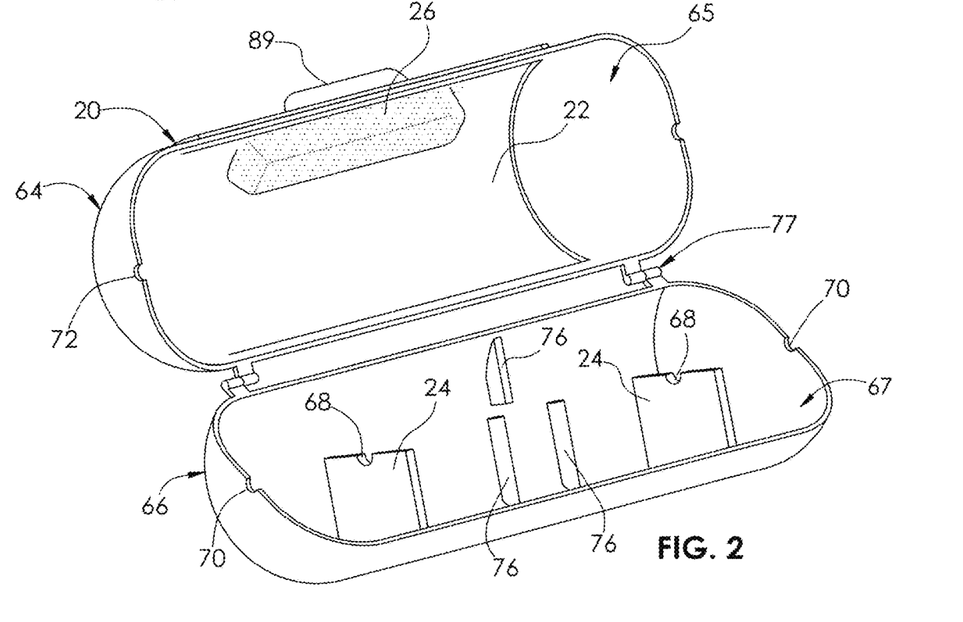
FIG. 2 shows a perspective view of the apparatus in FIG. 1 with the clam-shell body in the open position.
Figure 3:
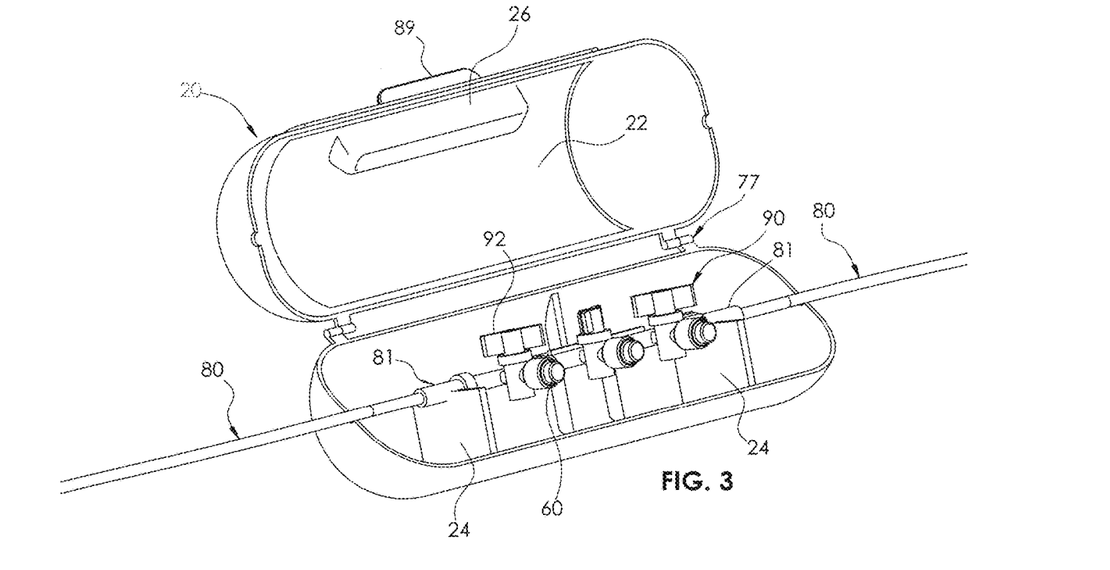
FIG. 3 shows a perspective view of the apparatus in FIG. 1 with the clam-shell body in the open position and an IV line with 3 ports present for reference.
Figure 5:
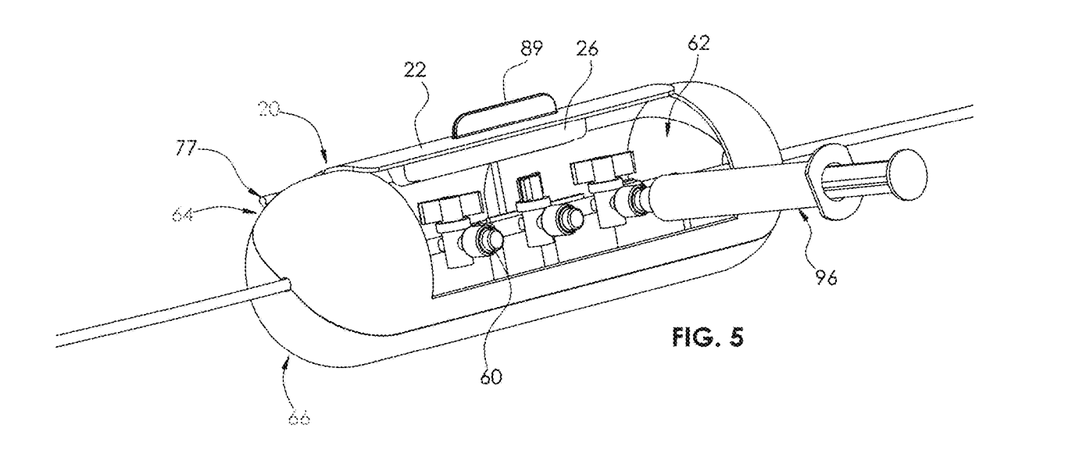
FIG. 5 shows a perspective view of the apparatus in FIG. 1 with the clam-shell body in the closed position and an IV line with 3 ports present for reference and the sliding door in the open position and a syringe for reference.
Figure 6:
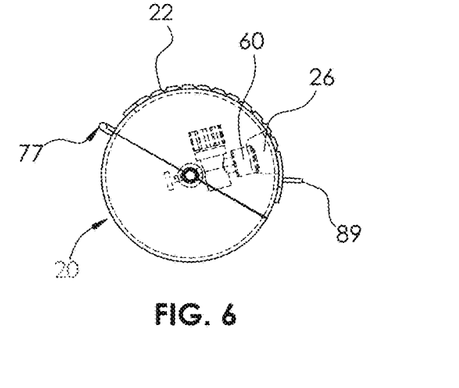
FIG. 6 shows an internal side view of the apparatus in FIG. 1.
Figure 7:
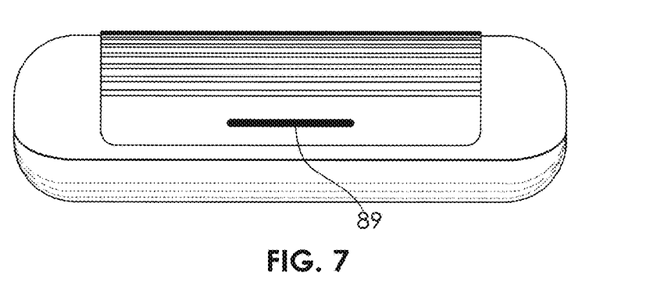
FIG. 7 shows a front view of the apparatus in FIG. 1.
Figure 8:
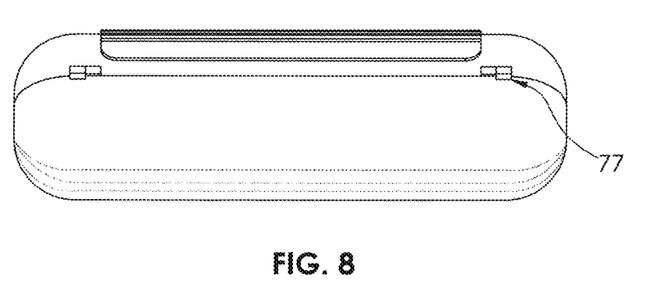
FIG. 8 shows a rear view of the apparatus in FIG. 1.
Figure 9:
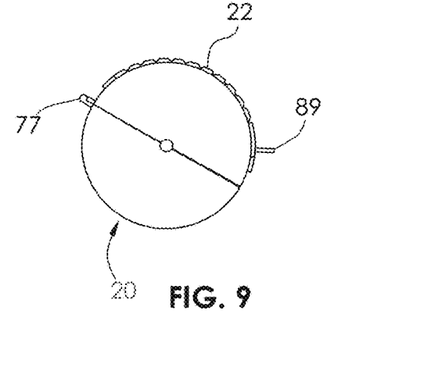
FIG. 9 shows a side view of the apparatus in FIG. 1.
Figure 10:
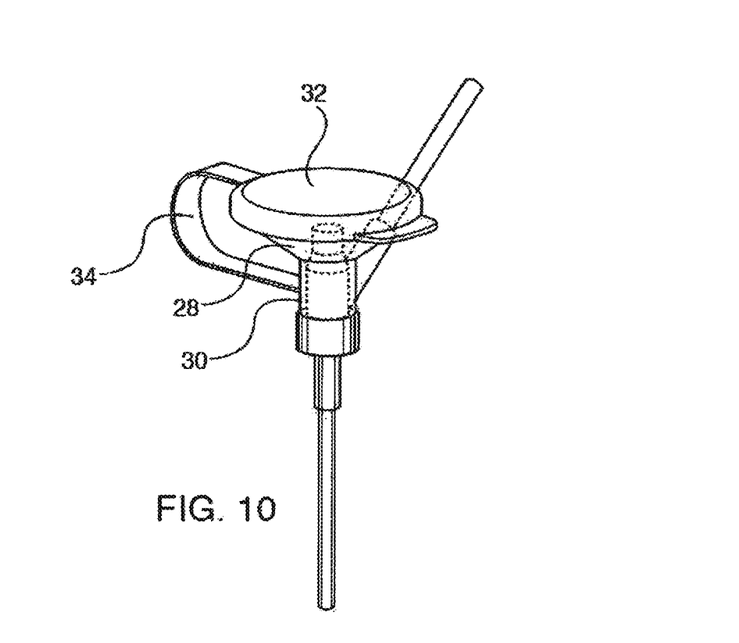
FIG. 10 shows an internal perspective view of an alternative apparatus embodying features of the present invention on top of a single access port for reference.
Figure 11:
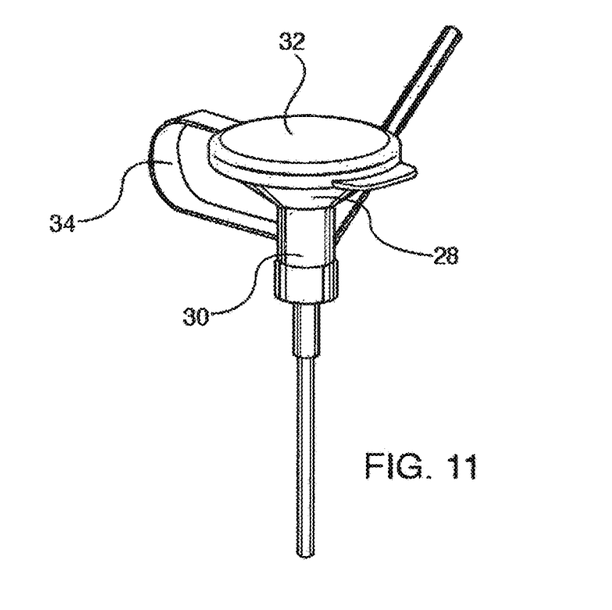
FIG. 11 shows a perspective view of the apparatus in FIG. 10.
Figure 12:
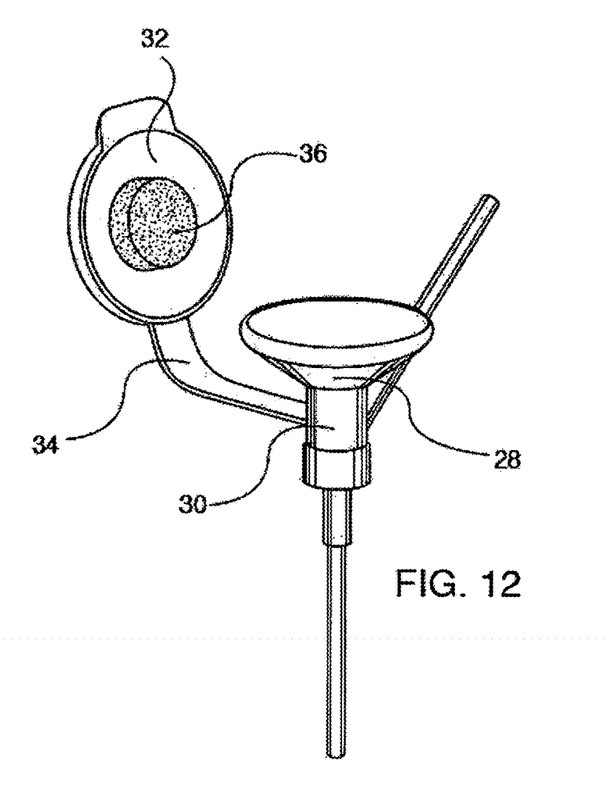
FIG. 12 shows a perspective view of the apparatus in FIG. 10 with the flip-top in the open position.
Figure 13:
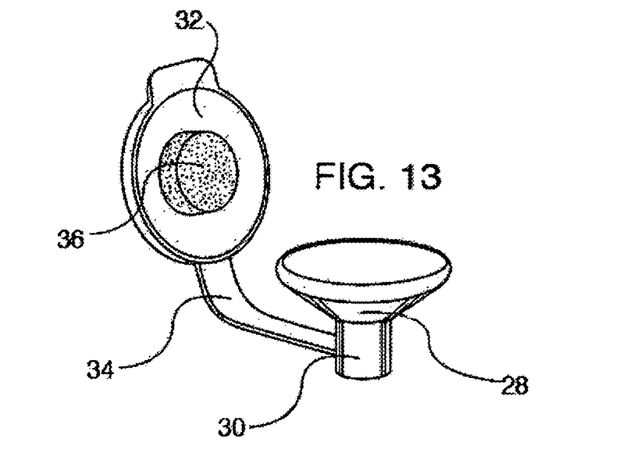
FIG. 13 shows a perspective view of the apparatus in FIG. 10 with no access port.
Figure 14:
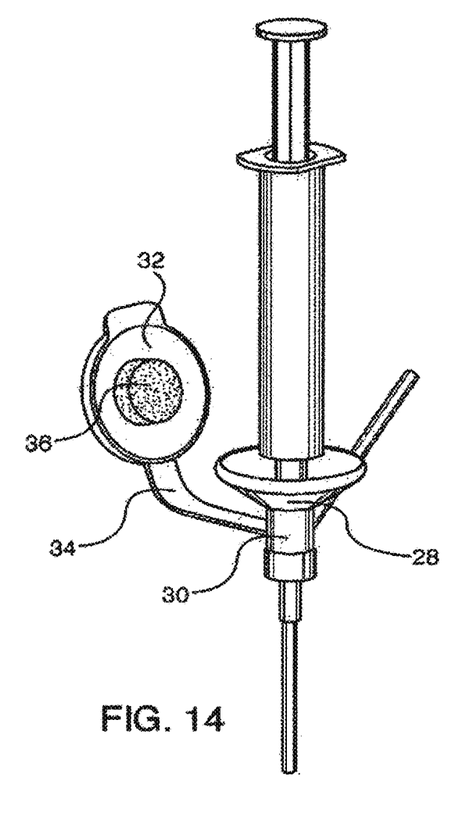
FIG. 14 shows a perspective view of the apparatus in FIG. 10 with the flip-top in the open position and a syringe for reference.
Figure 15:
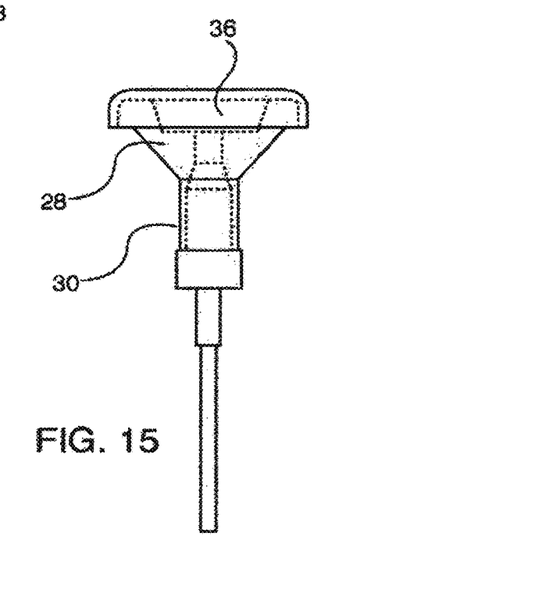
FIG. 15 shows an internal side view of the apparatus in FIG. 10.

As shown in FIG. 1, the apparatus of the present invention that may be marketed under the trade name "DefensIV", in one configuration, comprises a pill-shaped body 20 that includes a first body member 64 and a second body member 66 and a sliding cover or door 22 that, as shown in FIG. 5, helps define an opening 62 in the first body member 64. The first body member 64 also defines a pair of notches 72 spaced along a central longitudinal axis and sized to accommodate a standard IV tube 80, which is typically 3 or 4 mm in diameter and comprised of PVC, polyethylene, polypropylene, or similar polymeric material. As shown in FIG. 2, the second body member 66 defines a pair of notches 70 spaced along the central longitudinal axis and sized and positioned to accommodate a standard IV tube 80 in conjunction with the notches 72 defined by the first body member 64. The second body member 66 also includes an inner surface 67 form which at least one manifold support 24 extends therefrom and towards the central longitudinal axis. In one embodiment, each manifold support 24 defines a notch 68 that is sized and positioned to accommodate a standard IV tube 80 and/or tube fitting 81 in conjunction with the notches 72 defined by the first body member and the notches 70 defined by the second body member. According to one embodiment, the second body member 66 also includes at least one second manifold support 76 that extends from the second body member 66 and towards the central longitudinal axis. The second manifold supports 76 are sized and spaced to accommodate at least one IV manifold 90 (see FIG. 3) in conjunction with the notches 68, 70, and 72 that coordinate to receive and releasably secure an IV line 80 when the first body member 64 and second body member 66 are in a closed position. The first body member 64, and in on embodiment the cover 22, also includes a cushioned strip 26 extending radially inward from an inner surface 65 of the first body member 64. As shown in FIG. 10, the apparatus entitled "DefensIV", in another configuration, consists of a funnel-shaped body 28, a cylindrical connection 30, a flip-top cap 32, and a connector band 34. As shown in FIG. 12, the apparatus also consists of a cushioned disc 36.

Figure 4:
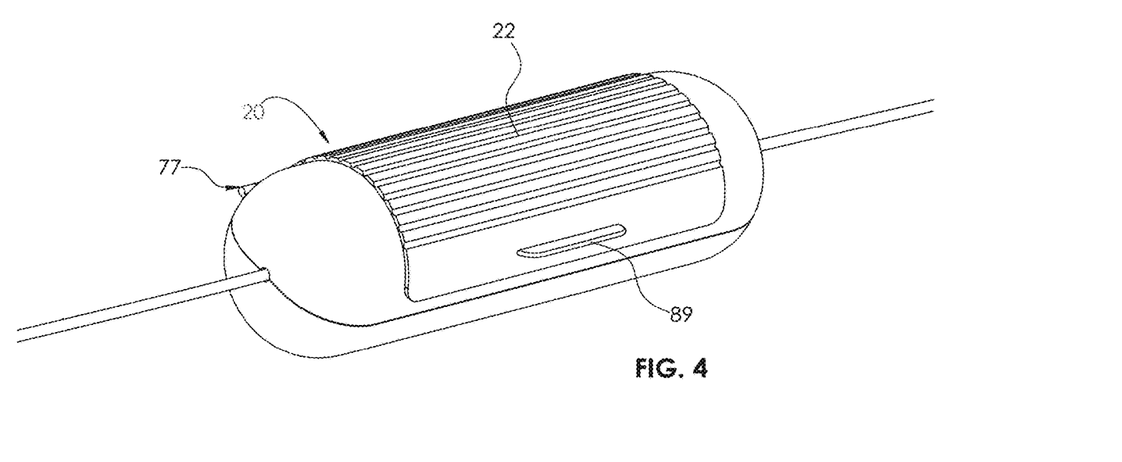
FIG. 4 shows a perspective view of the apparatus in FIG. 1 with the clam-shell body in the closed position and an IV line present for reference.

In a preferred embodiment of the invention the body 20 has an easy to handle and unobtrusive design and shape, such as an elongated pill-like shape, resembling a torpedo. One preferred material for the body 20 is lightweight plastic. However, any lightweight, shatter-resistant, clear, or opaque material similar in nature can be utilized from the components of the present invention. In addition, any of the materials utilized may include those that are microbe-resistant. As described herein, the IV manifold 90 includes at least one port 60 and valve adjuster 92 that are in fluid communication with the IV tube 80 and may be releasably inserted and secured into place between the first body member 64 and second body member 66 via the manifold supports 24 extending from inner surface 67 of the second body member 66, and then the first body member 64 and second body member 66 are moved from an open position, as shown in FIG. 2, to a closed position, as shown in FIG. 4, via a closure structure 77, such as a hinge. By way of explanation and not limitation, to closure structure 77 may take other forms and shapes beyond the hinge, such as an elongated hinge extending substantially along the length of the first body member 64 and second body member 66. Spring-loaded hinges could be used as the closure structure 77 to close and to keep the first body member 64 and second body member 66 closed under tension. Alternatively, a latching mechanism or inter-lock device may be used to facilitate closure of the first body member 64 and second body member 66. The first body member 64 also defines the opening 62 that is selectively covered by the cover 22. According to one embodiment, the cover 22 is slidably attached to the first body member 64 whereby the cover 22 acts similar to a garage door, in that it will operate along a curved track to align with the curve or radius of the first body member 64. The cover 22 may also be hingedly secured to the first body member 64 so that the cover 22 can move between an open position and closed position relative to the first body member 64. The cover 22 can open and close manually, such as by a user engaging a tab 89 that extends from the cover 22, to allow access and admission to the opening 62 and the IV access ports 60 of the manifold 90. At this time a syringe 96 can engage the port 60 to insert a fluid into the manifold 90. Advantageously, the port 60 has been enclosed and protected inside the closed device 20 between the first body member 64 and second body member 66, which minimizes the chance for bacterial growth and infection. Moreover, in one embodiment the port 60 has also been in contact with the strip 26 when the device 20 is in the closed position, which inhibits or retards bacteria growth and leaves the port at least substantially aseptic. In an alternative embodiment, the cover 22 can be biased to automatically close when not in use, such as by a spring. According to one embodiment, a cushioned, antiseptic strip 26 extends radially inward from the cover 22 and is positioned so that when the cover 22 is closed, the strip 26 will come into contact with the access ports 60, thereby keeping the access ports 60 and surrounding manifold surfaces substantially aseptic.

An alternate embodiment of the invention is for the main housing to be a funnel-shaped body 28 with a flip-top cap 32 on top. This funnel 28 will be attached to a cylindrical connection 30 which can attach to a single access port. The preferred material for funnel-shaped body 28 is lightweight plastic. However, any lightweight, shatter-resistant, clear, or opaque material similar in nature can be utilized for the components of the device. In addition, any of the materials utilized may include those that are microbe-resistant. When the flip-top cap 32 is closed the cushioned disc 36, located on the underside of the flip-top cap 32, will come into contact with the access port, thereby keeping the access port and surrounding hub surface essentially aseptic.

In either embodiment, the preferred method of manufacture of the components is injection molding, but could also be made by extrusion molding, blow molding, or rotational molding, or any number of similar manufacturing methods.

In a preferred embodiment, the strip 26 and the cushioned disc 36 are embedded with residual hydrogen peroxide (a zinc oxide based formulation that sequesters hydrogen peroxide and acts as an antimicrobial), but other liquid chemical treatments based in water, oil, or other solvents may be used, and additional scents, fresheners, antibiotics, antiseptic compounds, alcohols, proprietary chemicals, or other liquid ingredients could be added. Of the most common compounds known to those with skill in the art include without limitation 70% isopropyl alcohol, chlorhexidine gluconate, (CHG) 3.15%, and/or a combination thereof.

When access ports 60 are produced in multiple succession, this is known as a manifold 90. However, the length of the manifold 90 can be altered to accommodate a single port or multiple ports, depending on the design of the intravenous tubing 80. Any change in length, width, height, or depth of this device 20 will not be interpreted to be a departure from the subject matter claimed in this application.

The invention may be embodied in other forms without departing from the spirit and the essential attributes as described here. The particular embodiments described here explain several methods whereby a professional of reasonable skill might be able to replicate the invention but do not reduce the scope of the claims. Reference should be made to the appended Claims, rather than to the details of the Description here, in order to determine the scope of the invention.

What is claimed is:

1. A device for attaching to an intravenous port manifold having at least one port, comprising:
   a first body member and a second body member that are hinged along one edge and sized to receive and cover the entire port manifold, wherein at least one of the first body member and second body member defines an opening sized individually or in combination with an opening defined by the second body member the other opening to receive an intravenous fluid tube;
   a cover in communication with the first body member wherein the cover can be moved between a closed and an open position to expose an opening defined by the first body member and provide access to the intravenous port manifold;
   at least one manifold support extending from an inner surface of the second body member to releasably secure the port manifold; and
   an antiseptic strip extending radially inward from said cover such that said strip is capable of engaging the manifold when said cover is at least in the closed position.

2. A device for attaching to an intravenous port manifold having at least one port, comprising:
   a first body member and a second body member that are hinged along one edge and sized to receive and cover the entire port manifold, wherein at least one of the first body member and second body member defines an opening sized individually or in combination with an opening defined by the second body member the other opening to receive an intravenous fluid tube;
   a cover in communication with the first body member wherein the cover can be moved between a closed and an open position to expose an opening defined by the first body member and provide access to the intravenous port manifold, and
   an antiseptic strip extending radially inward from said cover such that said strip is capable of engaging the manifold when said cover is at least in the closed position.

3. A device according to claim 2, further comprising at least one manifold support extending from an inner surface of the second body member, wherein said at least one manifold support defines a notch sized to accommodate a portion of the port manifold.

4. A device according to claim 2, further comprising at least one manifold support extending from an inner surface of the second body member, wherein said at least one manifold support defines a notch sized to accommodate the intravenous fluid tube.

5. A method of enclosing an entire intravenous fluid manifold having at least one port and a pair of intravenous tubes extending along a longitudinal axis, comprising:
   placing the entire manifold between a first body member and a second body member, wherein the first body member and second body member are sized to receive and cover the entire port manifold and define openings along the longitudinal axis that are sized to accommodate and secure the intravenous tubes of the manifold when the first body member and second body member are moved into a closed position, closing the first body member and second body member so that an antiseptic strip extending from the first body member engages the at least one port of the manifold.

6. A method according to claim 5, wherein placing the entire manifold further comprises releasably securing the manifold against at least one manifold support extending from the second body member.

\* \* \* \* \*